US009347905B2

(12) United States Patent
Jiao et al.

(10) Patent No.: US 9,347,905 B2
(45) Date of Patent: May 24, 2016

(54) TRANSPARENCY HAVING MOISTURE SENSORS (71) Applicant: PPG INDUSTRIES OHIO, INC., Cleveland, OH (US)

(72) Inventors: Yu Jiao, Blawnox, PA (US); Nicolas Benjamin Duarte, Allison Park, PA (US); Jeremy D. Acord, Lower Burrell, PA (US)

(73) Assignee: PPG Industries Ohio, Inc., Cleveland, OH (US)

( * ) Notice: Subject to any disclaimer, the term of this patent is extended or adjusted under 35 U.S.C. 154(b) by 221 days.

(21) Appl. No.: 14/082,857

(22) Filed: Nov. 18, 2013

(65) Prior Publication Data
US 2015/0137837 A1    May 21, 2015

(51) Int. Cl.
*G01R 27/26* (2006.01)
*G01N 27/04* (2006.01)
*B32B 15/01* (2006.01)

(52) U.S. Cl.
CPC .............. *G01N 27/048* (2013.01); *B32B 15/01* (2013.01); *B32B 2255/06* (2013.01); *B32B 2255/26* (2013.01); *B32B 2307/202* (2013.01); *B32B 2605/18* (2013.01)

(58) Field of Classification Search
CPC .................... B32B 17/10036; G01N 5/025
USPC ........................................ 324/694, 689; 73/73
See application file for complete search history.

(56) References Cited

U.S. PATENT DOCUMENTS

| 3,867,837 | A | * | 2/1975 | Malin | .................... G01N 5/025 137/78.3 |
| 4,078,107 | A | | 3/1978 | Bitterice et al. | |
| 4,610,771 | A | | 9/1986 | Gillery | |
| 4,623,389 | A | | 11/1986 | Donley et al. | |
| 4,806,220 | A | | 2/1989 | Finley | |
| 4,820,902 | A | | 4/1989 | Gillery | |
| 4,894,513 | A | | 1/1990 | Koontz | |
| 4,902,875 | A | | 2/1990 | Koontz | |
| 4,994,650 | A | | 2/1991 | Koontz | |
| 5,659,294 | A | * | 8/1997 | Schroder | ............... B60S 1/0851 200/61.05 |

(Continued)

FOREIGN PATENT DOCUMENTS

| WO | 03/074334 A1 | 9/2003 |
| WO | 2004/050442 A2 | 6/2004 |
| WO | 2013/048698 A1 | 4/2013 |

OTHER PUBLICATIONS

A. de Rooij. "Bimetallic Compatible Couples", ESA Journal 1989, vol. 13, pp. 199-209.

(Continued)

*Primary Examiner* — Vincent Q Nguyen
(74) *Attorney, Agent, or Firm* — Andrew C. Siminerio (57) ABSTRACT

A transparency, e.g. an aircraft laminated windshield, includes one or more moisture sensors to monitor moisture penetration to monitor performance of the moisture barrier. The moisture sensor includes a moisture corrodible article or sensor element, e.g. a strip or wire, which changes resistance as a function of corrosion. The sensor element can also include two dissimilar metals, e.g. a bimetal sensor element, or two similar metals having different physical dimensions. With the information provided by the moisture sensors performance of the windshield is available to schedule timely repair or replacement of the windshield that is performing outside of acceptable limits.

18 Claims, 7 Drawing Sheets

(56) References Cited

U.S. PATENT DOCUMENTS

| | | |
|---|---|---|
| 5,675,944 A | 10/1997 | Kerr et al. |
| 5,821,001 A | 10/1998 | Arbab et al. |
| 7,231,727 B2 | 6/2007 | Kang et al. |
| 8,155,816 B2 | 4/2012 | Rashid et al. |
| 2005/0115308 A1* | 6/2005 | Koram ............. B32B 17/10036 73/73 |
| 2007/0002422 A1 | 1/2007 | O'Shaughnessy |
| 2007/0044542 A1 | 3/2007 | Barguirdjian et al. |
| 2010/0168935 A1* | 7/2010 | Rashid .................. B64C 1/1484 701/3 |

OTHER PUBLICATIONS

PCT Search Report, PCT/US2014/064010, dated Jan. 9, 2015.

* cited by examiner

TRANSPARENCY HAVING MOISTURE SENSORS

BACKGROUND OF THE INVENTION

1. Field of the Invention

This invention relates to transparencies, e.g. windows, having moisture sensors to measure ingress of moisture, and more particularly, to an aircraft or aerospace laminated window, e.g. an aircraft windshield having moisture sensors to monitor the real time performance of moisture seals of the window, and the amount of moisture accumulated over time.

2. Discussion of the Presently Available Technology

Aircraft or aerospace windows, e.g. aircraft windshields include a laminate of plastic layers or sheets, glass layers or sheets and combinations thereof. The layers of an inner segment of the windshield face the interior of the aircraft and are designed to provide structural stability to the windshield. The outer segment of the windshield faces the exterior of the aircraft and is designed to provide structural stability and accessories for visual acuity. For example and not limiting to the discussion, the accessories can included an electrically conductive coating, or a plurality of electrically conductive wires, between and connected to a pair of spaced bus bars to heat the windshield to prevent the formation of, and/or remove fog and ice on and/or from, respectively, the outer surface of the windshield.

As is appreciated by those skilled in the art, as the service time of the aircraft windshield increases, the operating efficiency of the windshield decreases until such time that the windshield becomes non-functional, and the windshield needs to be replaced or repaired. More particularly, the peripheral edge of the windshield has an outboard moisture seal that is a barrier to prevent moisture from entering between the plastic and glass layers or sheets of the windshield. When the moisture seal fails, e.g. cracks and/or the layers of the windshield laminate de-bond due to erosion caused by wind and rain, moisture enters between the layers of the windshield. While the cracking or de-bonding of the seal is not a structural issue, when moisture moves between the layers of the windshield, the windshield can de-laminate, and the conductive coating or wires, whichever is present can be damaged and fall, thereby reducing or ending, the service life of the windshield. More particularly, when delamination of the windshield occurs, increased amounts of moisture move between the layers of the windshield accelerating the degradation of the windshield, e.g. damage and/or failure of the bus bars and electrically conductive coating or wires, which reduces or eliminates the defrosting capabilities of the windshield.

Untimely response to repair defects in the accessories of the transparency when they begin, decreases the operating efficiency of the transparency and can result in the need for emergency maintenance, e.g. the repair or replacement of the transparency. It would be advantageous, therefore, to provide a transparency with moisture sensors to monitor the performance of the transparency so that the repair, or replacement, of the transparency is a scheduled maintenance and not an emergency maintenance.

SUMMARY OF THE INVENTION

This invention relates to a transparency including, among other things, a plurality sheets joined together; a sensor element responsive to moisture, the sensor element between the sheets; sensor electronics operatively connected to the sensor to measure an electrical property of the sensor that changes as a function of corrosion caused by moisture, wherein operatively connecting the sensor element and the sensor electronics to a power source to measure the electrical property of the sensor to determine if the sensor element is a new sensor element, an operating sensor element, a saturated sensor element, or a broken sensor element.

Further the invention relates to a method of determining life expectancy of a laminated aircraft transparency having moisture penetration, including, among other things, fabricating a laminated aircraft transparency having a moisture barrier over outer surface of the marginal edges of, and periphery of the laminated aircraft transparency; during fabrication of the laminated aircraft transparency placing a sensor element responsive to moisture between the sheets and/or between the sheets and the moisture seal of the aircraft transparency; operatively connecting sensor electronics to the sensor element to measure an electrical property of the sensor element that changes as a function of corrosion caused by moisture; operatively connecting the sensor element and the sensor electronics to a power source to measure the electrical property of the sensor to determine if the sensor element is a new sensor element, an operating sensor element, a saturated sensor element, or a broken sensor element, and replacing the aircraft transparency when the sensor element is at a predetermined value.

DETAILED DESCRIPTION OF THE INVENTION

As used herein, spatial or directional terms such as "inner", "outer", "left", "right", "up", "down", "horizontal", "vertical", and the like, relate to the invention as it is shown in the drawing on the figures. However, it is to be understood that the invention can assume various alternative orientations and, accordingly, such terms are not to be considered as limiting. Further, all numbers expressing dimensions, physical characteristics, and so forth, used in the specification and claims are to be understood as being modified in all instances by the term "about". Accordingly, unless indicated to the contrary, the numerical values set forth in the following specification and claims can vary depending upon the property desired and/or sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Moreover, all ranges disclosed herein are to be understood to encompass any and all subranges subsumed therein. For example, a stated range of "1 to 10" should be considered to include any and all subranges between and inclusive of the minimum value of 1 and the maximum value of 10; that is, all subranges beginning with a minimum value of 1 or more and ending with a maximum value of 10 or less, e.g., 1 to 6.7, or 3.2 to 8.1, or 5.5 to 10. Also, as used herein, the term "applied over", "positioned over" or "mounted over" means applied on, positioned on or mounted over but not necessarily in surface contact with. For example, one article or component of an article "applied over", "mounted over" or "positioned over" another article or component of an article does not preclude the presence of materials between the article, or between component of the article, respectively.

Before discussing several non-limiting embodiments of the Invention, it is understood that the Invention is not limited in its application to the details of the particular non-limiting embodiments shown and discussed herein since the invention is capable of other embodiments. Further, the terminology used herein to discuss the invention is for the purpose of description and is not of limitation. Still further, unless indicated otherwise, in the following discussion like numbers refer to like elements.

Non-limiting embodiments of the invention are directed to an aircraft laminated transparency, and in particular to an aircraft windshield. The invention, however, is not limited to any particular type of aircraft transparency, and the invention contemplates the practice of the invention on any type of windshield, e.g. but not limited to the laminated windshield disclosed in U.S. Pat. No. 8,155,816; the aircraft window having a medium responsive to electric stimuli to increase or decrease visible transmission, e.g. but not limited to the type of aircraft window disclosed in U.S. Published Patent application 2007/0002422A, and aircraft windows of the type having an insulated air space between a pair of laminated sheets. Further, the invention can be practiced on commercial and residential windows, e.g. but not limited to the type disclosed in U.S. Pat. No. 5,675,944; a window for any type of land vehicle; a canopy, cabin window and windshield for any type of air and space vehicle; a window for any above or below water vessel, and a window for a viewing side or door for any type of containers, for example but not limited to a refrigerator, cabinet and/or oven door. The documents identified herein are hereby incorporated by reference. Still further, the invention is not limited to the material of the layers or sheets of the transparency, and the layers or sheets can be made of, but not limited to, cured and uncured plastic sheets; annealed glass sheets, and heat and chemically strengthened, clear, colored, coated and uncoated glass sheets. As can now be appreciated, the invention can be practiced on windows having opaque sheets, e.g. but not limited to wood and metal sheets, and glass sheets having an opaque coating, and combinations thereof.

The aerospace windshield transparency is currently a passive component of the airplane with de-ice or de-fog features, however, it provides little to no feedback to the airplane system. The non-limited embodiments of the sensors of the invention provide an Intelligent window with the goal of providing feedback on the health status of the window system for electrical and mechanical integrity. Specifically, moisture ingress is a known problem of aerospace transparency aging, especially when window seals are not properly maintained. If left to continue, moisture ingress can permanently deteriorate the interior laminate, causing reduced visibility and rendering the window useless. In the worst cases, moisture ingress can affect the electrically conductive heater layer (discussed in detail below), potentially causing arcing and structure failure of one or more sheets or piles of the windshield.

Figure 1:
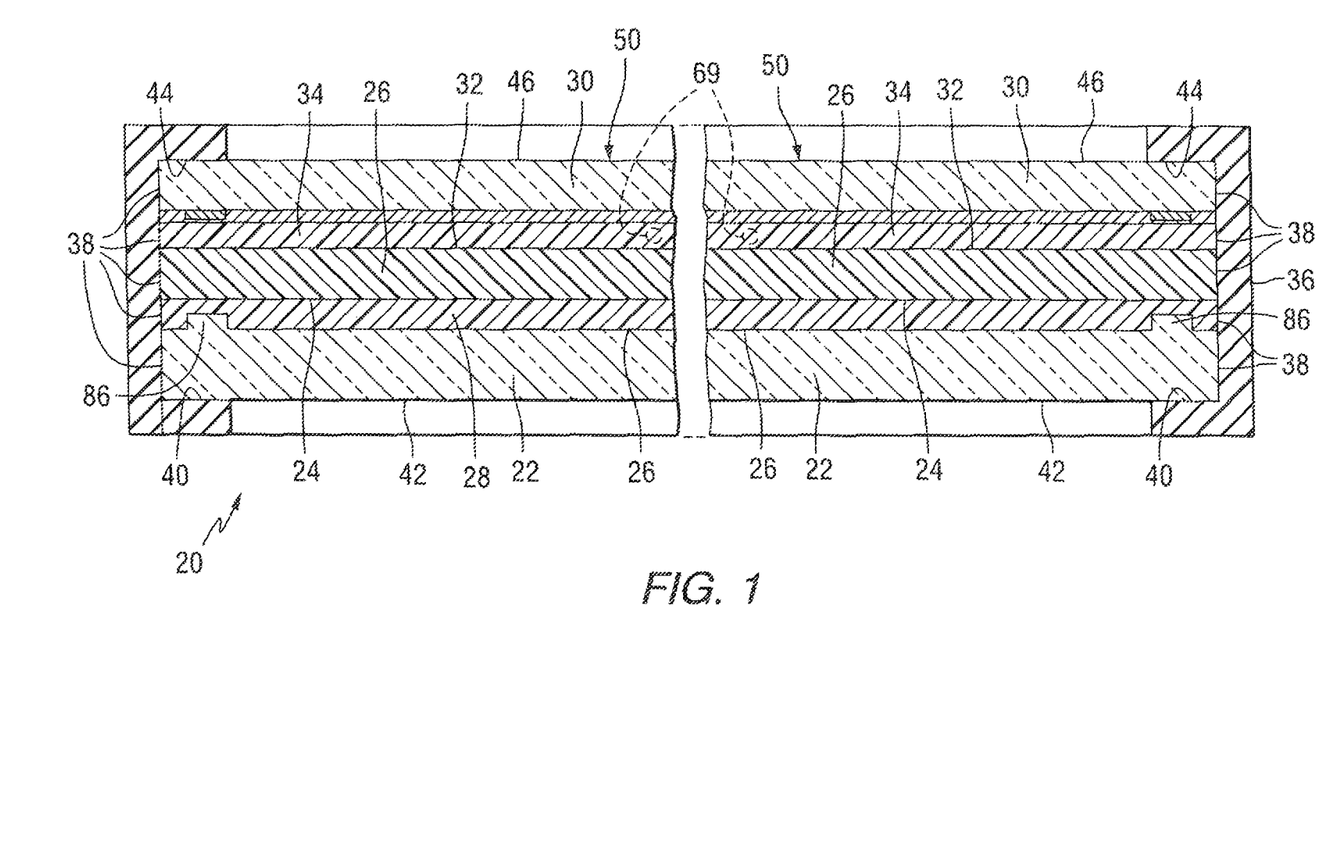
FIG. 1 is a cross sectional view of a non-limiting embodiment of an aircraft windshield incorporating features of the invention.

Shown in FIG. 1 is a non-limiting embodiment of an aircraft windshield 20 that can be used in the practice of the Invention. The windshield 20 has a first glass sheet 22 secured to surface 24 of a vinyl-interlayer or sheet 26 by a first urethane interlayer 28, and has a second glass sheet 30 secured to surface 32 of the vinyl-interlayer 26 by a second urethane interlayer 34. An edge member or moisture barrier 36 of the type used in the art, e.g. but not limited to a silicone rubber or other flexible durable moisture resistant material is secured to (1) peripheral edge 38 of the windshield 20, i.e. the peripheral edge 38 of the first and second sheets 22 and 30, respectively; of the vinyl-interlayer 26; of the first and second urethane interlayers 28 and 34, respectively; (2) margins or marginal edges 40 of outer surface 42 of the windshield 20, i.e. the margins 40 of the outer surface 42 of the first glass sheet 22 of the windshield 20, and (3) margins or marginal edges 44 of outer surface 46 of the windshield 20, i.e. margins of the outer surface 46 of the second glass sheet 30.

As is appreciated by those skilled in the art and not limiting to the invention, the first glass sheet 22; the vinyl-interlayer 26 and the first urethane interlayer 30 form the structural part, or inner segment, of the windshield 20. The outer surface 42 of the windshield 20, which is the outer surface 42 of the glass sheet 22 faces the interior of the vehicle, e.g. but not limited to an aircraft (aircraft shown in U.S. Pat. No. 8,155,816 B2). The second urethane layer 34 and the second glass sheet 30 form the non-structural part, or outer segment, of the windshield 20. The outer surface 46 of the windshield 20 which is the surface 46 of the second glass sheet 30 faces the exterior of the aircraft. The second glass sheet 30 is part of a heatable member 50 that provides heat to remove fog from, and/or to melt ice on, the outer surface 46 of the windshield 20 in a manner discussed below.

As can be appreciated the invention is not limited to the construction of the windshield 20 and any of the constructions of aircraft transparencies disclosed in the art can be used in the practice of the invention. For example and not limited to the invention, the windshield 20 can include a construction wherein the vinyl interlayer 28 and the first urethane interlayer 28 are omitted, and the glass sheets 22 and 30 are plastic sheets.

Generally the glass sheets 22, 30 of the windshield 20 are clear chemically strengthened glass sheets; however, the invention is not limited thereto, and the glass sheets can be heat strengthened or heat tempered glass sheets. Further as is appreciated, the invention is not limited to the number of glass sheets, vinyl interlayers or urethane interlayers that make up the windshield 20, and the windshield 20 can have any number of sheets and/or interlayers.

Figure 2:
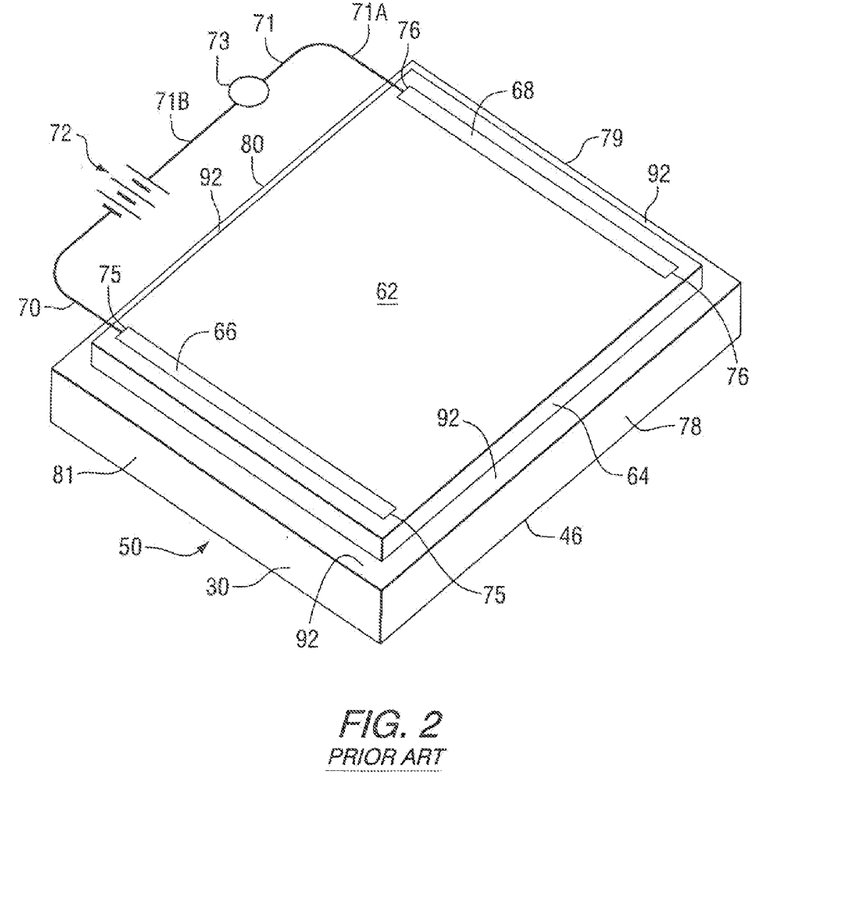
FIG. 2 is an isometric view of a prior art heatable member for removing fog, and melting ice and snow on the outer surface of the windshield.

The invention is not limited to the design and/or construction of the heatable member 50, and any electrically conductive heatable member used in the art to heat a surface of a glass or plastic sheet to melt ice on, and/or remove fog from the surface of the sheet can be used in the practice of the invention. With reference to FIG. 2, in one non-limiting embodiment of the invention, the heatable member 50 includes a conductive coating 62 applied to surface 64 of the second glass sheet 30, and a pair of spaced bus bars 66, 68 in electrical contact with the conductive coating 62. The Invention is not limited to the composition of the conductive coating 62, for example and not limiting to the invention; the conductive coating 62 can be made from any suitable electrically conductive material. Non-limiting embodiments of conductive coatings that can be used in the practice of the invention include, but are not limited to a pyrolytic deposited fluorine doped tin oxide film of the type sold by PPG Industries, Inc. under the trademark NESA®; a magnetron sputter deposited tin doped indium oxide film of the type sold by PPG Industries, Inc. under the trademark NESATRON®; a coating made up of one or more magnetron sputter deposited films, the films including, but not limited to a metal film, e.g. silver between metal oxide films, e.g. zinc oxide and/or zinc stannate, each of which may be applied sequentially by magnetron sputtering, e.g. as disclosed in U.S. Pat. Nos. 4,610,771; 4,806,220 and 5,821,001, the disclosures of which in their entirety are hereby incorporated by reference.

As can be appreciated, the invention is not limited to the use of an electrically conductive coating to heat the glass sheet 60 and contemplates the use of any type of member that can be electrically heated, e.g. but not limited to electrical conducting wires. The wires, e.g. the wires 69 shown in phantom in FIG. 1 can be embedded in the second urethane interlayer 34 and electrically connected to the bus bars 66 and 68. Such a heating arrangement is known in the art under the PPG Industries Ohio Inc. registered trademark AIRCON and is disclosed in U.S. Pat. No. 4,078,107, which patent in its entirety is incorporated herein by reference.

The invention is not limited to the design and/or construction of the bus bars and any of the types of bus bars known in the art can be used in the practice of the invention. Examples of bus bars that can be used in the practice of the invention, include, but are not limited to, the types disclosed in U.S. Pat. Nos. 4,623,389; 4,820,902; 4,894,513; 4,994,650, and 4,902875, which patents in their entirety are hereby incorporated by reference. Each of the bus bars 66 and 68 are connected by a wire 70 and 71, respectively to a power source 72, e.g. a battery to flow current through the bus bars 66 and 68, and the conductive coating 62 to heat the conductive coating 62 and the second glass sheet 30 to remove ice and/or fog from the outer surface 46 of the windshield 20. A window heat controller 73 to provide electrical current to heat the coating 62 and to disconnect electrical current from the coating 62 is connected to one of the wires, e.g. the wire 71 such that wire section 71A of the wire 71 connects one pole of the window heat controller 73 to the bus bar 68, and the wire section 71B of the wire 71 connects another pole of the window heat controller 73 to the battery 72. With this arrangement, the window heat controller 73 can control the electrical power to the bus bars 66 and 68, and the conductive coating 62 to vary or regulate the current flow through the bus bars 68 and 66, and the conductive coating 62 to control the temperature of the conductive coating 62. Although not limiting to the invention, ends 75 of the bus bar 66, and ends 76 of the bus bar 68 are spaced from adjacent sides 78-81 of the glass sheet 30 to prevent arcing of the bus bars 66 and 68 with the metal body cover of the aircraft 47.

Figure 3:
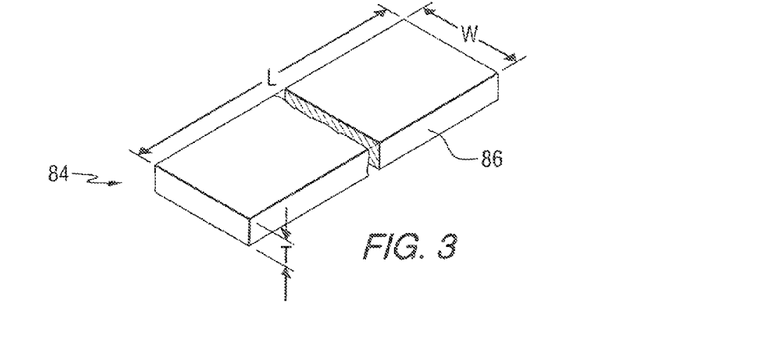
FIG. 3 is an Isometric view of a non-limiting embodiment of a moisture sensor or detector of the invention.

A non-limiting embodiment of a moisture sensor of the invention is shown in FIG. 3 and designated by the number 84. The moisture sensor 84 includes an electrically conductive, moisture corrodible strip 86 securely mounted on a surface of one or more of the sheets 22 and 30, the vinyl interlayer 26 and/or one or both of the urethane layers 28 and 34 of the windshield 20 in a manner discussed below. The strip 86 is made of a material that conducts electricity; Is corroded or dissolves in the presence of moisture; the corrosion and dissolving of the strip changes an electrical property of the strip, e.g. but not limited to the impedance and/or ohm resistance of the strip 86, and the material of the strip 86 is inert to the material in which the strip is imbedded, e.g. but not limited to the vinyl interlayer 26, and the urethane interlayers 28 and 34. In a non-limiting embodiment of the invention, the corrosion and/or the dissolving of the strip 86 reduces the cross sectional area of the strip 86 which changes an electrical property of the strip, e.g. but not limited to the impedance and/or ohm resistance of the strip. With continued reference to FIG. 3, for purposes of clarity, the Invention is not limited to the length (designated by "L"), width (designated by "W") or thickness (designated by "T") of the strip 86. The cross sectional area of the strip 86 is equal to the W times T. As can now be appreciated, increasing the L of the strip 86 provides for increasing the distance covered by the strip 86; increasing the W and T of the strip 86 increases the useable life of the strip, and increasing the T of the strip 86 increases the life of the strip 86.

Materials that can be used in the practice of the invention include, but are not limited to iron, chromium and aluminum. In the preferred practice of the invention, the conductive strip 86 is a carbon steel strip. Further, the conductive strip 90 can be a conductive coating material formed from a ceramic paint or electrically conductive ink. The conductive material in the preferred practice of the invention is a material that will deteriorate, e. g. will rust or dissolve when contacted with moisture and produce an electrical change, e.g. but not limited to a change in the electrical resistance as the amount of rust changes.

The purpose of the moisture measurement is not simply to measure the instantaneous water ingression rate between sheets of the aircraft laminated windshield, but also the quantity of moisture accumulated over time. The history of the moisture ingression is just as important as the absolute concentration of the water in the window system. The concept of the window moisture measurement is based on the electrical property changes of a sensor element following moisture (water) ingression between the sheets of the windshield. A sensor system includes, but is not limited to, the sensor element together with the electrical power supply, circuitry and software that detects the changes and communicates the changes to the persons responsible for maintaining the aircraft in a safe operating condition, e.g. as disclosed in U.S. Pat. No. 8,155,816 B2, which patent is hereby incorporated by reference.

In one non-limiting embodiment of the invention, the sensor element is based on the predictable increase in resistance of a metallic wire or metallic strip due to corrosion of the strip in the presence of moisture. While a sensor element of a single metal or alloy strip can increase in resistance predictably, eventually the current flow through the wire will decrease to zero as one position on the wire corrodes completely away. Additionally, such a zero current state is indistinguishable from a mechanical failure of the sensor that was not related to a moisture ingression event, e.g. but not limited to a fracture of the glass supporting the sensor. Finally, because of the slow reaction of the single metal corrosion, the electrical resistance changes due to the moisture ingression may not be significant enough for a real world moisture sensor application.

Figure 4:
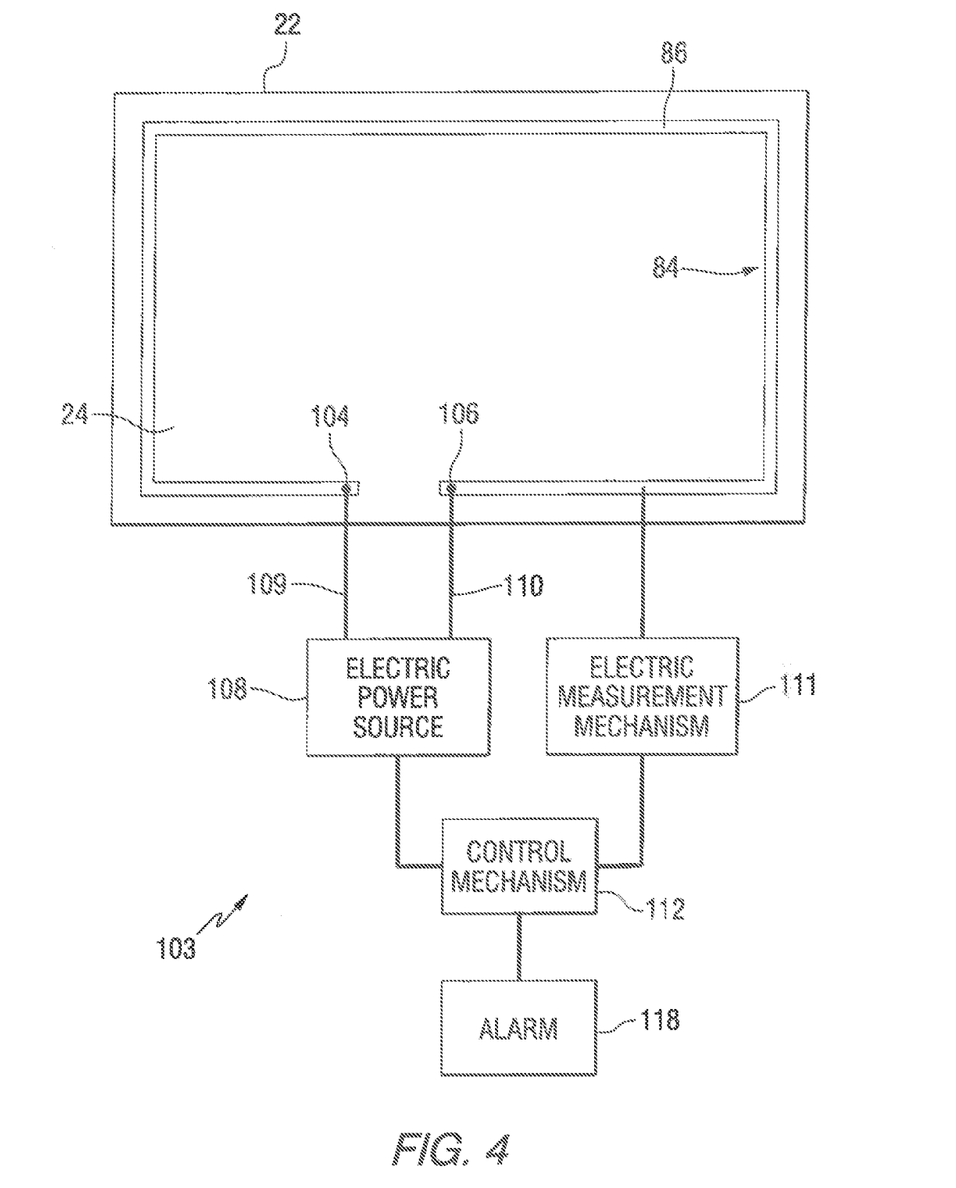
FIG. 4 is a non-limiting embodiment of an electrical system to monitor and act on the output signals of the moisture sensor in accordance to the teachings of the invention.

The invention is not limited to the circuit employed to measure the electrical changes when moisture begins corroding or dissolving the sensor 84 (see FIG. 3). Shown in FIG. 4 is a non-limiting embodiment of an electrical system 103 that can be used with the sensor 84 to determine moisture penetration of the windshield 20. In the non-limiting embodiment of the invention shown in FIG. 4, the strip 86 of the moisture sensor 84 is applied to the surface 24 of the glass sheet 22 and secured against the surface 24 in any usual manner, e.g. but not limiting to the invention by the first urethane interlayer layer 28 (see FIG. 1). As can be appreciated, the strip 86 can be applied to any surface of any one of the glass sheets 22 and 30, and vinyl interlayer 26 of the laminated windshield 20. In the non-limiting embodiment of the invention shown in FIG. 4, the conductive strip 86 is mounted over the surface 24 of the first glass sheet 22 and extends around substantially the entire marginal edges of the first glass sheet. The conductive strip 86 has a first termination surface 104 and a second termination surface 106. The distance or gap between the first termination surface 104 and the second termination surface 106 should be sufficient to prevent any descriptive electrical field communication between the termination surfaces 104 and 106.

The termination surfaces 104 and 106 are connected to an electrical power source 108 of the electrical system 103 by leads or wires 109 and 110 to apply an electrical potential to the strip 86. The power source 108 can be any conventional electrical source, such as, but not limited to, a battery, an electrical generator, and the like. Further, the strip 86 of the moisture sensor 84 includes an electrical measurement mechanism 111, such as an ohmmeter, in communication with the conductive strip 86 for measuring the electrical potential of the strip 84. A control mechanism 112, such as software and a computer, is used to control and communicate with both the electrical power source 108 and the electrical measurement mechanism 111. This control mechanism 112 can be used to command the electrical power source 108 to provide a predetermined or specifically set electrical potential to the conductive strip 89 and, after application, the control mechanism 112 can collect and/or calculate the electrical potential of the strip 86 via the electrical measurement mechanism 111. All of the electrical power source 108, the electrical measurement mechanism 111 and the control mechanism 112 can be combined in a single unit or instrument, e.g. a console of the type shown in FIG. 18 of, and disclosed in, U.S. Pat. No. 8,155,816 B2 or can be individual units (see FIG. 4).

The electrical power source 108 applies a set voltage to the strip 86, as set or specified by the control mechanism 112. This set voltage allows current to flow through the strip 86. As mentioned above, the electrical power source 108 is connected to the strip 86 through a first lead 109 and a second lead 110. The first lead 109 is connected to the first termination surface 104, and the second lead 110 is connected to the second termination surface 106. This connection allows the conductive strip 86 to act as an electrical circuit when the electrical power source 108 applies an electrical potential.

The electrical measurement mechanism 111 reads or measures the current flowing through the strip 90 via the first lead 114 connected to the first termination surface 104, and the second lead 116 connected to the second termination surface 106. Since the electrical power source 108 is applying a set voltage, and the electrical measurement mechanism 110 is reading or measuring the current flowing through the strip 86, the electrical measurement mechanism 111 (or the control mechanism 112) is able to calculate the resistance value of the strip 86 to indicate the loss of the strip 86 as a result of moisture corroding or dissolving the strip 86.

More particularly, when moisture penetrates the windshield 20, the moisture will eventually reach the conductive strip 86. As the moisture reaches the strip 86 it begins to corrode or dissolve the strip 86 increasing the resistance of the strip 86. As the strip continues to corrode or dissolve, the strip eventually has a void, which is indicated as infinite resistance or an open, and indicates serious moisture penetration. Optionally, when the resistance of the strip 86 is at a predetermine value, the control mechanism 112 sends a signal to the alarm 118 to advise the crew of the aircraft and/or other personnel as disclosed in U.S. Pat. No. 8,155,816 B2 of a moisture penetration issue.

The conductive strip 86 of the electrical system 103 shown in FIG. 4 can be used to indicate that moisture has penetrated the area between the glass sheet 22 and the vinyl interlayer 26 (see FIG. 1), however using a single strip 86 does not indicate where the moisture penetration occurred how far the moisture has penetrated, or which side of the windshield the moisture has penetrated. In order to enhance identifying the moisture penetration areas between the glass sheet 22 and the vinyl interlayer 26, multiple strips can be placed in a grid or array pattern over the inner surface 24 of the sheet 22.

Figure 5:
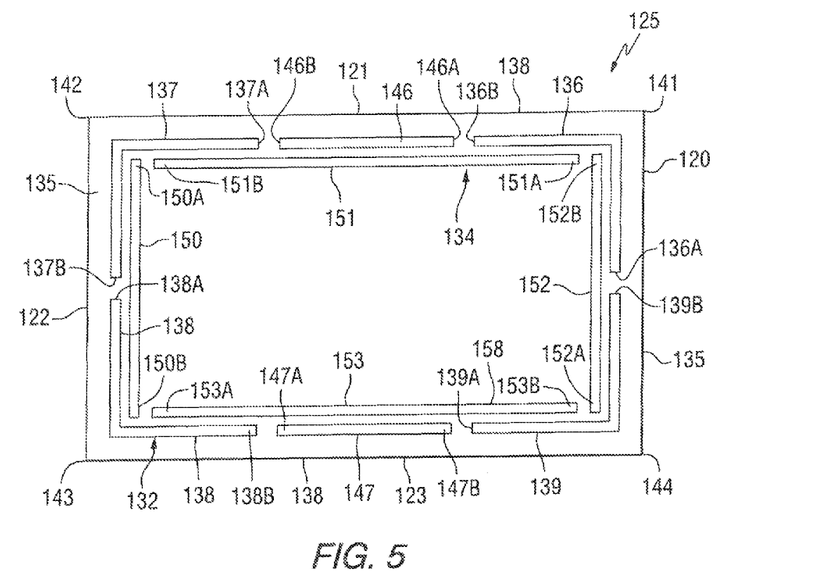
FIG. 5 is a plan view of a non-limiting embodiment of an arrangement of moisture sensors or detectors to estimate approximate position of moisture penetration and depth of moisture penetration.

In the non-limited embodiment of the invention shown in FIG. 5, each one of sides 120-123 of glass sheet 125 has two rows 132 and 134 of stripes 86 at or adjacent margin 135 of glass sheet 125 to provide an array of conductive stripes to more definitively identify where a moisture area in the windshield is present. Although the non-limited embodiment of the invention under discussion references the sheet 125 (FIG. 5), the discussion is applicable to the glass sheets 22 and 30, the vinyl interlayer 26 and urethane interlayers 28 and 34 unless indicated otherwise. The first row 132 of the conductive stripes includes conductive stripes 136-139 at the corners 141-144, respectively of the sheet 125, and conductive strips 146 and 147 at the sides 121 and 123, respectively of the sheet 125. With continued reference to FIG. 5, end 136A of the strip 136 is adjacent to and spaced from end 139B of the strip 139 at the side 120 of the sheet 125; end 136B of the strip 136 is spaced from and adjacent to end 146A of the strip 146, and end 146B of the strip 146 is adjacent to and spaced from end 137A of the strip 137, at the side 121 of the sheet 125; end 137B of the strip 137 is adjacent to and spaced from the end 138A of the strip 138 at the side 122; end 1388 of the conductive strip 138 is adjacent to and spaced from end 147A of the strip 147, and end 147B of the strip 147 is adjacent to and spaced from end 139A of the strip 139, at the side 123, of the sheet 125.

The second row 134 of the conductive strips includes conductive strips 150-153. The conductive strip 150 extends between sides 121 and 123 of the glass sheet 125; has its end 150A adjacent to and spaced from end 151B of the strip 151, and its end 150B adjacent to and spaced from end 153A of the strip 153. The conductive strip 151 extends between sides 122 and 120 of the glass sheet 125 and has its end 151A adjacent to and spaced from end 152B of the strip 152. The conductive strip 152 extends between sides 121 and 123 of the glass sheet 125 and has its end 152A adjacent to and spaced from end 153B of the strip 153. The conductive strip 153 extends between sides 120 and 122 of the glass sheet 125 and has its end 153B adjacent to and spaced from end 152A of the strip 152.

The ends A and B of each of the strips 136-139, 146, 147 and 150-153 are individually electrically connected to the electrical power source 108 (see FIG. 4) to apply an electrical potential to the conductive strips 136-139, 146, 147 and 150-153, and to the electrical measurement mechanism 111 for measuring the electrical potential of the conductive strips 136-139, 146, 147 and 150-153. The control mechanism 112 controls and communicates with both the electrical power source 108 and the electrical measurement mechanism 111 as discussed above to command the electrical power source 108 to provide a predetermined or specifically set electrical potential to the conductive strips 136-139, 146, 147 and 150-153 and, after application, the control mechanism 112 can collect and/or calculate the electrical potential of the conductive strip 136-139, 146, 147 and 150-153 via the electrical measurement mechanism 111. All of the electrical power sources 108, the electrical measurement mechanisms 110 and the control mechanisms 112 for the conductive stripes 136-139, 146, 147 and 150-153 can be combined in a single unit or instrument, e.g. a console of the type disclosed in U.S. Pat. No. 8,155,816 B2, or can be individual units.

With continued reference to FIG. 5, the arrangement of the two rows 132 and 134 each having spaced conductive strips, e.g. stripes 136-139, 146 and 147 in the row 132, and the conductive stripes 150-153 in the row 134 provides for a closer approximation to area of moisture penetration. More particularly and not limiting to the invention, moisture attacks the conductive strips 146 and 151, positioning moisture penetration 156 in the center area of the side 121 of the sheet 125; moisture attacks the conductive strips 139 and 153, positioning the moisture penetration 158 in the side 123 adjacent the side 138 of the sheet 125.

The conductive strip 86 can be applied to a surface of one or more of the glass sheets 22, 24, 28 and 60. As is appreciated, when a conductive strip is placed on more than one sheets, each one of the conductive strips 86 preferably has its own electrical power source 108, or one power source is provided and is electrically connected to two or more of the conductive strips 86, and a rheostat is provided for each conductive strip 86 for controlling voltage to each of the conductive strips 86. Similarly, one or multiple electrical measurement mechanisms 110 can be used to read and measure the electrical potential or current flowing through each of the conductive strips 90 on the sheets 22, 24, 28 and 60 of the windshield 20. In this manner the output of each of the moisture sensors on the glass sheets 22, 24, 28 and 60 can be monitored.

Figure 6:
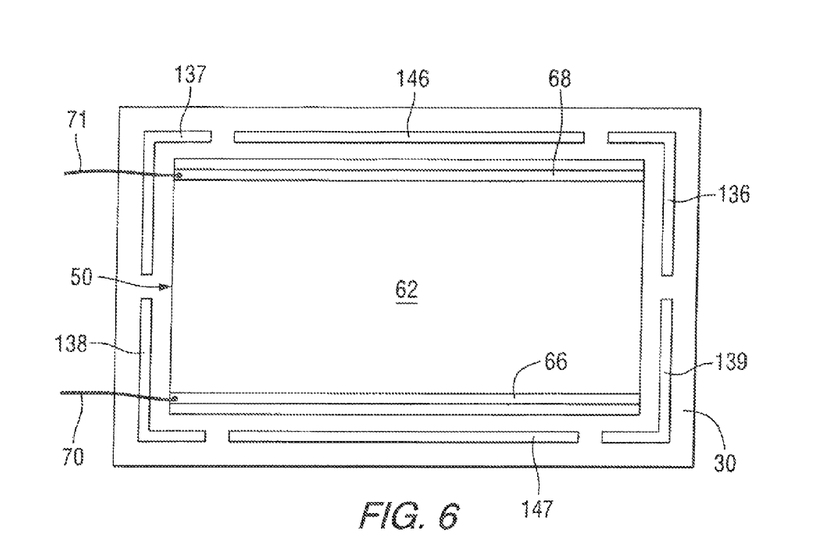
FIG. 6 is a plan view showing the moisture sensor of the invention surrounding the heatable member shown in FIG. 2.

With reference to FIG. 6, there is shown the heatable member 50 applied to the inner surface of the second glass sheet 30. As can be appreciated by those skilled in the art, the conductive stripes 136-139, 146 and 147 of the sensor 84 are electrically isolated from the bus bars 66 and 68, and from the conductive coating 62, of the heatable member 50. In one non-limiting embodiment of the invention, the bus bars are within the coating 62 and the coating 62 is spaced from the sides of the glass sheet. The strips 136-139, 146 and 147 are applied on the surface of the glass sheet between the edge of the sheet and the heatable member 62. The uncoated glass strip 102 can be provided in any convenient manner, e.g. by masking the glass surface during the coating process, or abrasively or chemically removing the coating from the glass surface. Because the glass is chemically strengthened it is preferred to mask the areas during the coating process to avoid surface damage that can cause the tempered glass to fracture.

Figure 7:
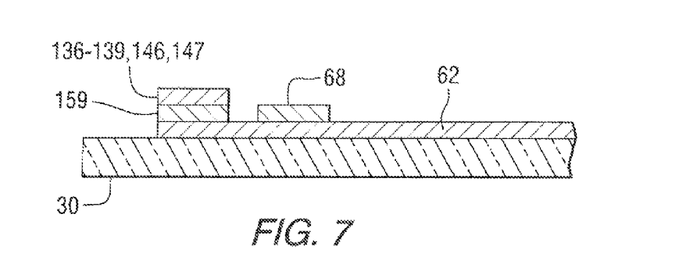
FIG. 7 is an elevated cross sectional side view showing a non-limiting embodiment of the Invention for mounting a sensor over a bus bar of a heatable member.

In another non-limiting embodiment of the invention shown in FIG. 7, the electrically conductive coating 62 extends under the strips 136-139, 146 and 147, and the coating 62 and the strips 136-139, 146 and 147 are electrically insulated from one another by a layer of a non-conductive material, e.g. but not limited to plastic 159. The layer 159 can have an adhesive layer on each surface to secure one of the metal strip 136-139, 146 and 147 in position on the conductive coating 62 during the laminating process. As can be appreciated, the conductive strip can decrease visibility through that portion of the glass sheet over which it is deposited, and therefore, for the metal strips that extend into the vision area of the windshield, the maximum width of the metal strip 86 depends upon the required or specified operator viewing area through the windshield 20. Aircraft transparencies, e.g. windshields have specific safety requirements specifying the viewable (or transparent) area required.

Although single metal strips for use as moisture sensors are acceptable, it is noted that they are slow. In those instances when the response using a single metal strip for a moisture sensor has a slow reaction, e.g. the electrical resistance changes due to the moisture ingression may not be significant enough for a real world moisture sensor application, bimetallic sensors are preferred.

In this non-limiting embodiment of the invention, the predictable response of a bimetallic sensor element is used. The bimetallic sensor, includes, but is not limited to two dissimilar metals in close contact, so as to form a single sensor element. In particular, dissimilar metals in electrical contact may undergo galvanic corrosion in the presence of moisture. Galvanic corrosion (also called bimetallic corrosion, electrochemical corrosion, and dissimilar metal corrosion) is defined as an electrochemical process in which the rate of corrosion of one metal in a pair will be faster than the other member of the pair when both metals are in electrical contact and Immersed in a corrosive solution or atmosphere. In general the corrosion reactions that occur in a coupled bimetal are similar to those that would occur on the individual un-coupled metals, but the rate of corrosion of one metal is increased, sometimes dramatically, while the other metal can corrode gradually or be completely protected. The galvanic corrosion reaction is broken up into two largely independent processes: 1) transfer of metal into the solution with an equivalent number of electrons left in the metal, called the anodic process, and 2) assimilation of the excess electrons in the metal, called the cathodic process. (cite A. de Rooij, "Bimetallic Compatible Couples" ESA Journal 1989, Vol. 13 PP 199-209). The two processes are typically localized in different regions, most typically between dissimilar metals in electrical contact with each other.

The tendency of a metal to give up electrons in a solution is measured as a voltage (potential) with respect to a reference electrode, typically either the saturated calomel electrode or the standard hydrogen electrode. The potentials of common metals and alloys can be found in published tables as a galvanic series for a particular set of conditions, arranged in order of increasing electronegativity. Typically the more electropositive metal becomes cathodic with respect to the more electronegative metal, which is preferentially corroded. It should be noted that the values of the potentials for any pair of metals can be influenced by a variety of factors, including but not limited to type of electrolyte, temperature, pH and the ratio of the surface areas of the two metals in the pair. This can, under particular circumstances, lead to a reversal of the anodic and cathodic reactions in the pair; that is, the metal that corroded readily under one set of conditions may become protected under another set of conditions. No generally valid galvanic formula can be written to predict a priori the behavior of a specific pair of metals under a particular set of conditions. Thus the selection of suitable metal pairs for a particular application is often based on prior experience. While much research has been reported on the topic of minimizing the corrosion of bimetallic couples, in this non-limiting embodiment of the invention the metals should be selected to enhance the corrosion rate of the anodic wire, providing a predictable sensor output that occurs at a rate consistent with the design life of the sensor.

The discussion is now directed to design considerations for bimetallic sensor elements.

Figure 8:
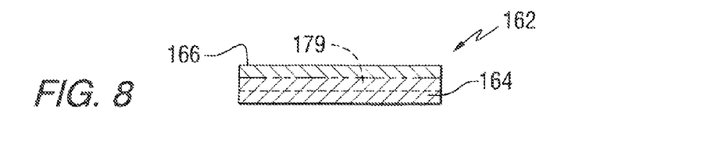
FIG. 8 is a side elevated view of a non-limited embodiment of a sensor of the invention having two similar metals of different physical dimensions.

Shown in FIG. 8 is a non-limited embodiment of a bimetallic moisture sensor designated by the number 162. The sensor 162 includes a first strip 164 and a second strip 166. The first strip 164 and the second strip 166 have the same or different cross sectional area, and are made of different materials such that the strips 164 and 166 of the sensor 162 corrode and/or dissolve at different rates. With this arrangement the sensor 162 can provide information regarding the rate of corrosion. In one non-limiting embodiment of the invention, the first strip 164 of the sensor 162 can be made of zinc, and the second strip 166 of the sensor 162 can be made of iron.

Ideally, the response of a bimetallic sensor element should be designed by selecting particular constituent metals to: a) maximize the measurable increase in resistance of the bimetallic sensor element and b) match the response time of the bimetallic sensor element to the window life. In practice, selection of materials will also be influenced by price and availability of the materials, compatibility with the manufacturing process and the Federal Aviation Administration ("FAA") certification process.

The first consideration is the factors affecting the resistance change of the sensor element. The electrical resistance of the bimetallic sensor element can be modeled as a resistor network consisting of both series and parallel elements, with the points of electrical contact between the two wires represented as nodes on the network and the resistance of each wire segment between the contact points as parallel resistors. Prior to the start of corrosion, the starting resistance of the bimetallic sensor element can be calculated from the individual resistances as:

$$R_0 = \frac{R_{anodic} \times R_{cathodic}}{R_{anodic} + R_{cathodic}}$$

where $R_{anodic}$ is the starting resistance of the anodic metal wire, $R_{cathodic}$ is the starting resistance of the cathodic metal wire and $R_0$ is the starting resistance of the bimetallic sensor element. As a simplification for the purpose of Illustrating the design principles, corrosion resulting in the complete removal of the anodic wire (prior to the onset of corrosion in the cathodic wire) will cause the sensor resistance to increase to a value of:

$$R_{bimetal\_corroded} = R_{cathodic}$$

The simplified expression for the maximum possible change in sensor element resistance is equal to:

$$\Delta R_{limit} = \frac{R_{bimental\_corroded} - R_0}{R_0} = \frac{R_{cathodic}}{R_{anodic}}$$

And the sensor resistance as a function of time is:

$$R_{sensor} = \{1 + f(\text{cathodic potential, anodic potential, area ratio, pH, moisture, etc.}) \times t\} R_0$$

From this simplified model it is readily apparent that the sensor metals should be selected to maximize the starting resistance of the cathodic wire and minimize the starting resistance of the anodic wire. In general a high resistivity metal that is on the cathodic end of the galvanic series should be chosen for the cathodic wire, and the diameter minimized (provided the surface area of the cathode relative to the anode remains sufficiently large to support the cathodic reaction at a desirable rate). Conversely, the ideal anodic wire should have a low resistivity, should be more anodic on the galvanic series and should have a relatively larger starting diameter.

When combined with the considerations in the previous paragraph, specific combinations of metals can be "smart selections" that will improve the sensor capability. One possible "smart" combination that has been proven in the laboratory is an anodic iron wire with a cathodic chromel (90% nickel/10% chromium) resistance wire. The iron wire has an electromotive force ("EMF") of approximately −0.52 volts ("V") (value for mild steel, relative to saturated calomel electrode, in 3.5% NaCl solution) while the chromel has a potential of −0.10 V in the passive corrosion mode and −0.27V in the active corrosion mode (values are for 80% nickel/20% chromium alloy). Since the iron is more electronegative than the chromel under most circumstances, it will be preferentially corroded while the chromel will be "protected". Annealed iron wire has a resistivity of 60 ohm per circular-mils/foot, while chromel is over seven times higher (425 ohm per circular-mils/foot). Iron wires initially tested were 0.001 inch (1 mil) and 0.010" (10 mil) in diameter. Chromel wires initially tested were 0.005" (5 mil), 0.015" (15 mil) and 0.020" (20 mil) in diameter. This smaller diameter iron wire started off with a higher resistance and tended to respond rapidly, while the larger diameter allows a greater overall change in sensor resistance over a longer time.

Pairs of wires tested included Iron/Zinc; Chromel/Iron; Chromel/Aluminum; Chromel/Zinc; Iron/Copper; Nikrothal/Iron; Cuprothal/Iron; Kanthal/Iron, and Nifethal/Iron.

In summary and in one non-limiting embodiment of the invention, there are three selection criteria for wires used in the bimetal sensor:
  Resistivity: A high resistivity wire is desirable for the cathodic wire to define the final sensor resistive point and provide greater sensitivity. A low resistivity wire is desirable for the anodic wire to allow the greatest change in resistance upon corrosion. This parameter needs to be correlated with the diameter in order to achieve an appropriate final resistance.
  Diameter: The anodic wire should be selected to be larger diameter than the cathodic wire to facilitate the chemical reaction.
  Galvanic Potential: Wires should be paired to be on the opposite ends of the galvanic potential spectrum to allow the greatest reaction possibility. This is not a strict requirement because exceptions occur with some metal pairs that have close galvanic potentials that result in fast electrochemical corrosion rates.

In operation, there are four states of sensor conditions.
1) New sensor: In this state the sensor maintains the original resistance and does not show any change in resistance over time.
2) Operating sensor: When exposed to moisture, the sensor resistance will change over time.
3) Saturated/consumed sensor: Once the cathode is consumed the resistance will reach a saturation point and there is no further change in resistance. This type of reaction is expected for a sensor having an anode and a cathode with electrical reaction.

4) Broken sensor: In the case of a broken wire due to a bad connection, mechanical damage, etc., the resistance of the sensor will read as a new sensor or an operating sensor and read as infinite resistance. This is one of the advantages of the invention since it distinguishes between a saturated/consumed sensor and a broken sensor. More particularly, the cathode corrodes faster than the anode. The cathode has separation resulting from corrosion, and the anode is still intact. The cathode has infinite resistance and the anode has less resistance. If there is a bad connection, the anode and the cathode have infinite resistance.

Figure 9:
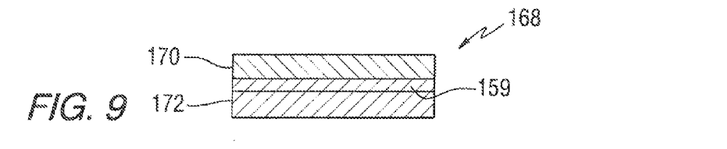
FIG. 9 is a side elevated view of another non-limited embodiment of a sensor of the invention having two dissimilar metals.

Shown in FIG. 9 is still another non-limited embodiment of a moisture sensor of the invention designated by the number 168. The sensor 168 includes a first strip 170 and a second strip 172 joined together by the electrically insulating layer 159. The first strip 170 and the second strip 172 can have different cross sectional areas, or can have the same cross sectional area, and can be made of the same material. The sensor 168 can be positioned between two sheets with the strip 170 facing a first sheet and the strip 172 facing an opposite second sheet. The corrosion rate of the strips 170 and 172 can be used to estimate the ingress of moisture, e.g. the ingress between the strip 170 and the first sheet, and the strip 172 and the second sheet.

Figure 10:
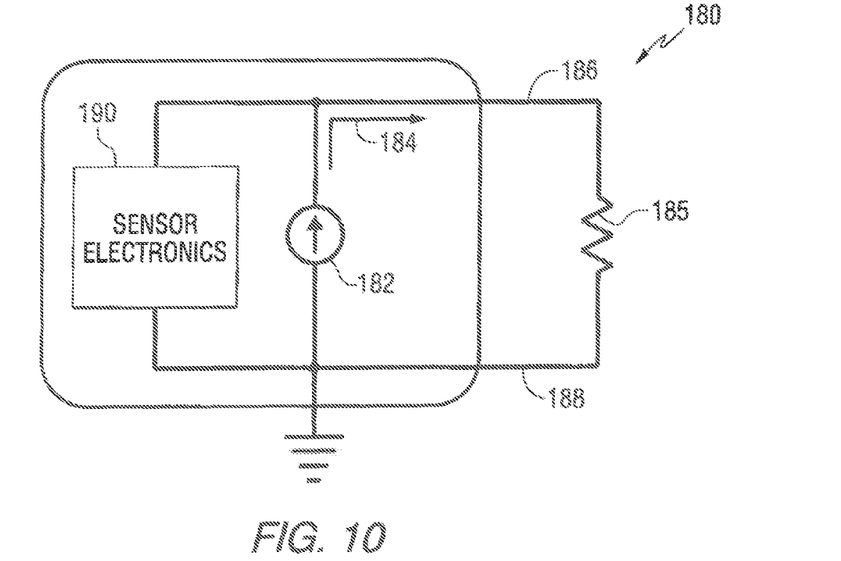
FIG. 10 is a non-limiting embodiment of a read out circuit that can be used in the practice of the invention.
Figure 11:
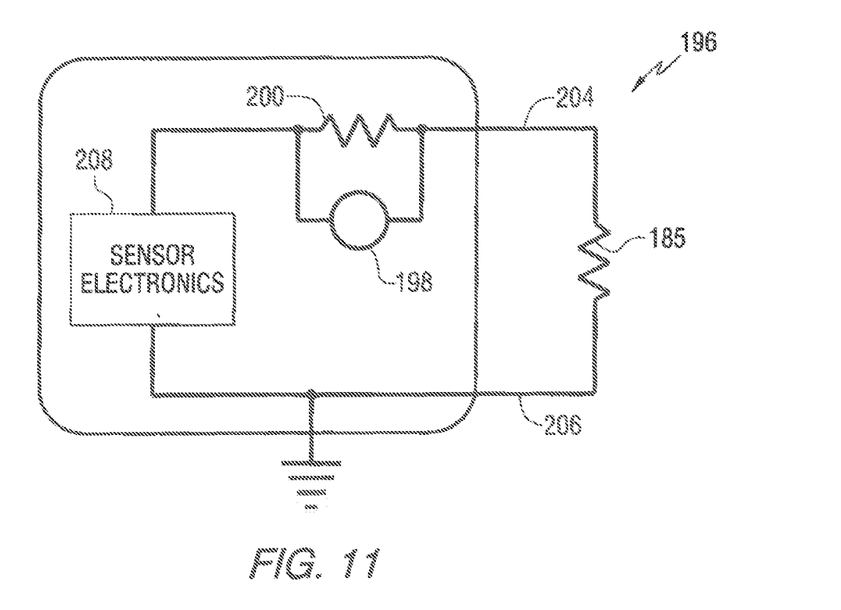
FIG. 11 is another non-limiting embodiment of another read out circuit that can be used in the practice of the invention.

In one non-limited embodiment of the invention, the bimetallic stripes 164 and 166 of the sensor 162 are electrically connected to one another by a conductive adhesive 179 (shown in phantom in FIG. 8). The resistance of the bimetallic moisture sensor element can be measured using a variety of standard readout sensor circuits, two classes of which are depicted in FIGS. 10 and 11. The first class of readout circuits is shown in FIG. 10 and identified by the number 180. The circuit 180 includes a current source 182 that drives a fixed current 184 through the circuit containing a sensor 185 of the invention, e.g. but not limited to the sensors 82, 162 or 168 connected by wires 186 and 188. As the resistance of the sensor element 185 increases the voltage generated across the sensor element increases in direct proportion. The voltage across the sensor element is read directly by the sensor electronics 190. In this type of circuit the starting resistance of the sensor can be used as a reference to indicate the zero moisture state, and any finite increase in the resistance will indicate the presence of moisture. As mentioned above, if the sensor element or the circuit 180 is broken the resistance will drop to zero, indicating a failed state.

The second broad class of readout circuits is shown in FIG. 11 and identified by the number 196. The circuit 196 includes the second broad class of readout circuits, and employs a voltage source 198, which will apply a known voltage across the circuit 196. The circuit 196 further includes a known reference resistor 200, the sensor element 185 and the connecting wires 204 and 206. The voltage will divide across the resistances in series in proportion to their resistances. The voltage across the reference resistor 200 is read directly by sensor electronics 208. As the resistance of the sensor element 202 increases the voltage across the reference resistor 200 will decrease. The value of the reference resistor 200 can be adjusted to produce a preferred starting value in the zero moisture state, allowing the manufacturer to compensate for sensor variations. A broken sensor element or connecting wire will cause the voltage to fall to zero, indicating a failed state.

The discussion is now directed to non-limited embodiments of the Invention relating to the placement of the non-limiting embodiments of moisture sensors or detectors of the invention on selected components of the windshield 20, to detect the presence of moisture and/or measure the amount of moisture present between the sheets, e.g. but not limited to, between the glass sheets 22 and 30, in accordance to the teachings of the invention.

As discussed above and as shown in FIG. 1, the windshield or transparency 20 has an outboard moisture barrier or seal 36 to prevent or reduce moisture penetration between the first and the second glass sheets 22 and 30, respectively; the vinyl interlayer 26, and the first and the second urethane interlayers, 28 and 34, respectively. More particularly, when the moisture seal 36 fails, e.g. cracks or de-bonds due to erosion caused by wind and rain, moisture enters between the glass sheets 28 and 30 of the windshield 20. While the cracking or de-bonding of the moisture seal 36 is not a structural issue, when moisture moves between the glass sheets 28 and 30, the windshield 20 can de-laminate, and/or the heatable member 50 can be damaged and fall, reducing the service life of the windshield. When delamination of the windshield 20 occurs, the rate and amount of moisture entering between the glass sheets 22 and 30 of the windshield increases, accelerating the degradation of the windshield. Practicing the non-limiting embodiments of the invention monitors the moisture penetration between the glass sheets 22 and 30 of the windshield 20, and provides information that can be analyzed to determine the condition and/or performance of the moisture barrier 36, and provides for replacement or repair of the moisture barrier 36 before degradation of the windshield 20 caused by moisture penetration begins or accelerates.

Figure 12:
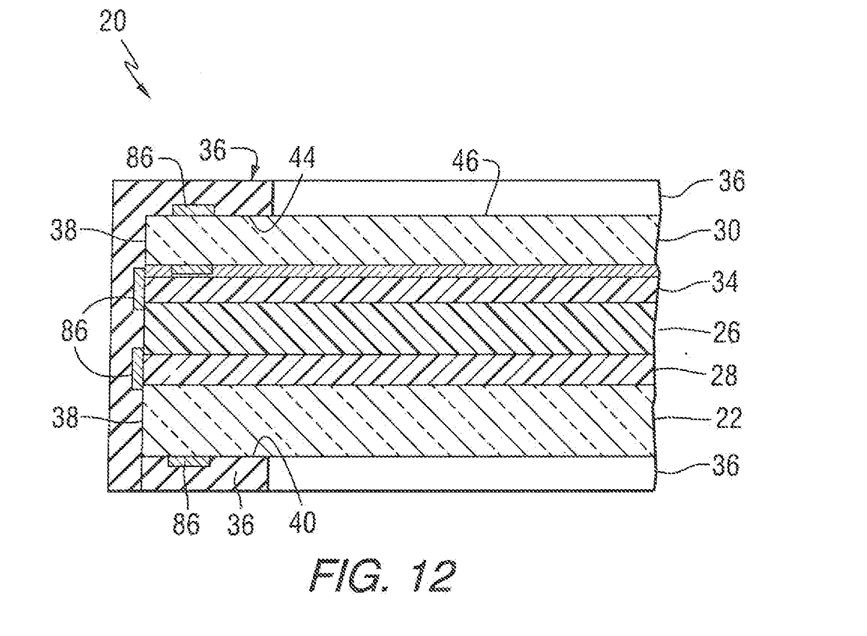
FIG. 12 is a cross section view of a segment of the windshield shown in FIG. 1 showing the position of moisture sensors or detectors at the marginal and peripheral edge portions of the aircraft windshield in accordance to the teachings of the invention.

As critical as the measurement principle and type, where the moisture sensor should be located will determine if the new sensor can effectively detect the moisture ingress and provide early enough warning for the "Intelligent Window" sensor system to alarm the pilot. With reference to FIG. 12 as needed, the placement of the strip 86 (FIG. 4) or multiple strips (FIGS. 5 and 6) can be applied to any position on or between the glass sheets 22 and 24, and the vinyl interlayer 26. Further, the invention is not limited to the number of strips 86 of the sensor and the location of the strips 86 on the windshield. More particularly and not limiting to the invention, the strip 86 can be embedded in the first urethane layer 28 between the glass sheet 22 and the vinyl interlayer 26; embedded in the second urethane layer 28 between the glass sheet 30 and the vinyl interlayer 26; between the moisture barrier 36 and the marginal edges of the first glass sheet 22, between the moisture barrier 36 and the marginal edges of the second sheet 22; between the moisture barrier 36 and the peripheral edges of the windshield.

Figure 13:
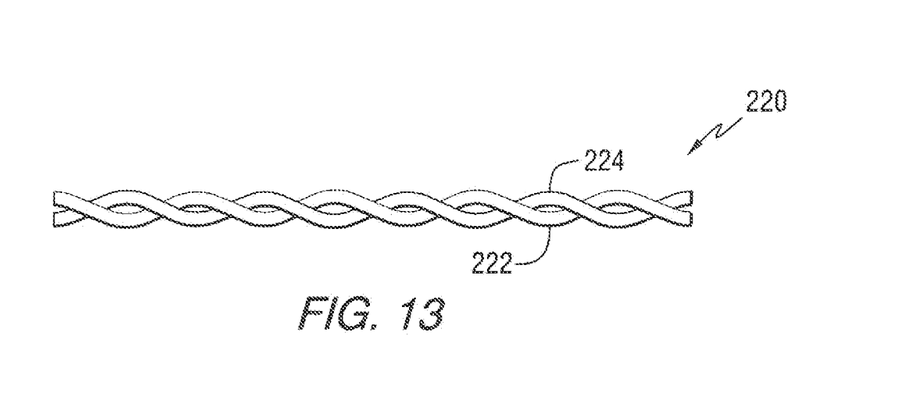
FIG. 13 is a plan view of another non-limiting embodiment of a moisture sensor of the invention.

The Invention is not limited to the shape of the sensor strip or element of the moisture sensor of the invention. For example and not limiting to the invention, the sensor elements or strips discussed above had an elongated shape with a square or rectangular cross section. The invention, however contemplates sensor elements or strips made of any shape, e.g. but not limited to elongated shape with a circular cross section. More particularly, shown in FIG. 13 is a sensor element 220 having a pair of wires 222 and 224 twisted around one another. The wires 222 and 224 can be used alone for a one wire sensor element, can be of different materials for a bimetallic sensor element, or can be of the same material but different sizes as discussed above.

In the non-limited embodiments of the invention discussed above, the sensor 86, in general, has the sole function of measuring the presence and time period that moisture is in contact with the sensor 86. The invention, however, is not limited thereto, and the sensor of the invention can be used to measure the presence and time period that moisture is in contact with the sensor 86 and to activate and deactivate electrical equipment, e.g. as discussed below and in U.S. Pat. No. 8,155,816 B2.

Control System

Disclosed in U.S. Pat. No. 8,155,816 is method and apparatus to monitor the performance of a transparency, e.g. but not limited to the windshield 20 of the invention and to timely schedule maintenance of, e.g. repairs to, or replacement of, transparencies, e.g. aircraft windshields that are performing outside acceptable limits. In this particular instance, performing outside of acceptable limits as a result of moisture penetration.

In general the output of the sensors carrying data regarding the performance of moisture barrier of the windshield are connected to a console including a computer having software to read and analyze the signals from the sensors or detectors to monitor and/or determine the performance of the windshield. A monitor can be used in the practice of the invention to provide visual display, and a speaker to provide an audio, regarding the performance of the windshield. The console can include an alarm to bring attention to the monitor. Placing the console in the aircraft provides the personnel within the aircraft with real time performance of the windshield.

In another embodiment disclosed in U.S. Pat. No. 8,155,816, the console has a wireless transmitter and receiver; the transmitter transmits signals to a transmitting tower. The signals carry data on the performance of the windshield 20 are transmitted to a control center 324. The data received is studied and the appropriate action to be taken is scheduled, e.g., based on the information received, personnel at the control center determine what action, if any, is needed. If action such as repairs to the windshield or replacement of the windshield, is needed, a signal providing a repair schedule is transmitted to the satellite to a maintenance center geographically close to the designated repair location (usually the next scheduled stop for the aircraft) to arrange to have all parts, equipment and personal need at the designated repair location.

In another embodiment of U.S. Pat. No. 8,155,816, if the data from the sensors indicate that the windshield 20 has to be replaced, the repair schedule can include shipment of the windshield to the next scheduled stop of the aircraft; If the windshield has to be replaced with some urgency, the repair schedule would include a change to the flight plan to land immediately and a windshield will be there, or will arrive shortly. The passengers can optionally be transferred to another plane, or wait until the repair is completed. If a repair is scheduled, and the repair can be made without removing the windshield, the repair schedule can provide for personnel and repair parts to be provided at the designated repair location.

The invention is not limited to the embodiments of the Invention presented and discussed above which are presented for illustration purposes only, and the scope of the invention is only limited by the scope of the following claims and any additional claims that are added to applications having direct or indirect lineage to this application.

What is claimed is:

1. An aircraft transparency comprising:
a plurality of sheets joined together;
a moisture seal overlaying marginal edges of outer opposed surfaces, and peripheral edge, of the aircraft transparency, and the sensor element between the sheets and/or between the sheets and the moisture seal;
sensor element responsive to moisture, the sensor element between the sheets, wherein the sensor element is a first elongated moisture sensor having a first end and a second opposite end, and comprising second, third, and fourth elongated moisture sensors; each of the moisture sensors comprising a first end and an opposite second end, wherein the first, second, third and fourth moisture sensors are mounted on a major surface of one of the pair of sheets adjacent peripheral edge of the sheet, wherein the second end of the first sensor is adjacent and spaced from the first end of the second sensor, the second end of the second sensor is adjacent and spaced from the first end of the third sensor, the second end of the third sensor is adjacent and spaced from the first end of the fourth sensor, and the second end of the fourth sensor is adjacent and spaced from the first end of the first sensor;
sensor electronics operatively connected to the sensor to measure an electrical property of the sensor that changes as a function of corrosion caused by moisture, wherein operatively connecting the sensor element and the sensor electronics to a power source to measure the electrical property of the sensor to determine if the sensor element is a new sensor element, an operating sensor element, a saturated sensor element, or a broken sensor element.

2. The transparency according to claim 1, wherein the transparency is an aircraft transparency and each of the sheets comprises a first major surface opposite to a second major surface and a peripheral surface joining the first major surface, wherein the second surface of the first sheet is in facing relationship to and spaced from the second surface of the second sheet and the sensor element is between the first sheet and the second sheet, and spaced from the peripheral edge of the first sheet and the second sheet.

3. The transparency according to claim 1 comprising:
the plurality of sheets comprises two or more transparent sheets joined together by an adhesive, and
the sensor element on a surface portion of at least one of the sheets.

4. The transparency according to claim 3 wherein each of the sheets comprises a first major surface opposite to a second major surface and a peripheral surface joining the first major surface and the second major surface, wherein the surface portion of the at least one of the sheets is selected from the group of the first major surface, the second major surface, the peripheral surface and combinations thereof.

5. The transparency according to claim 3, wherein the sensor element is a pair of wires twisted around one another.

6. The transparency according to claim 5 wherein the first, second, third and fourth elongated sensors form a first boundary and comprising a second boundary within and spaced from the first boundary, and a third boundary within and spaced from the second boundary, wherein each of the second and third boundaries comprises at least one elongated moisture sensor defined as a fifth elongated moisture sensor for the second boundary and the sixth elongated moisture sensor for the third boundary.

7. A transparency comprising;
a plurality of sheets joined together;
sensor element responsive to moisture, the sensor element between the sheets, wherein the sensor element is a metal strip that corrodes in the presence of moisture, and the ohm resistance measured increases as the corrosion increases;
sensor electronics operatively connected to the sensor to measure an electrical property of the sensor that changes as a function of corrosion caused by moisture, wherein operatively connecting the sensor element and the sensor electronics to a power source to measure the electrical property of the sensor to determine if the sensor element is a new sensor element, an operating sensor element, a saturated sensor element, or a broken sensor element.

8. The transparency according to claim 7 wherein the sensor element includes two strips of the same metal having different widths.

9. The transparency according to claim 7, wherein the transparency is selected from the group of a laminated aircraft transparency, commercial and residential windows, a window for any type of and vehicle; a canopy, cabin window and windshield for any type of air and space vehicle, a window for any above or below water vessel, and a window for a viewing side or door for any type of containers.

10. The transparency according to claim 9 wherein the sheets of the transparency are selected from the group of uncured plastic sheets; annealed glass sheets, and heat and chemically strengthened, clear, colored, coated and uncoated glass sheets.

11. A transparency comprising:
a plurality of sheets joined together;
a sensor element responsive to moisture, the sensor element between the sheets, wherein the sensor element is a bimetallic strip of two metals that corrodes in the presence of moisture, and the ohm resistance of each of the two metals measured increases as the corrosion increases and the ohm resistance of each metal differs;
sensor electronics operatively connected to the sensor to measure an electrical property of the sensor that changes as a function of corrosion caused by moisture, wherein operatively connecting the sensor element and the sensor electronics to a power source to measure the electrical property of the sensor to determine if the sensor element is a new sensor element, an operating sensor element, a saturated sensor element, or a broken sensor element.

12. The transparency according to claim 11 wherein the bimetallic strips is selected from the groups of pairs of wires comprises Iron/Zinc; Chromel/Iron; Chromel/Aluminum; Chromel/Zinc; Iron/Copper; Nikrothal/Iron; Cuprothal/Iron; Kanthal/Iron, and Nifethal/Iron.

13. The transparency according to claim 11 wherein the strips overlay one another and are electrically isolated from one another.

14. The transparency according to claim 11 wherein the strips overlay one another and are electrically connected to one another.

15. The transparency according to claim 11 wherein one of the strips is a cathodic strip and other one of the strips is a anodic strip, and the cathodic strip has a resistivity higher than the resistivity of the anodic strip, and the anodic strip has a width greater than the width of the cathodic wire.

16. The transparency according to claim 11 wherein the bimetallic strips are paired to be on the opposite ends of the galvanic potential spectrum to allow the greatest reaction possibility.

17. The transparency according to claim 11 wherein the sensor element is one of a plurality of sensor elements, wherein a first one of the plurality of sensor elements is between the moisture seal and the sheets, and a third one of the plurality of sensor elements is between the moisture seal and outer surface portion of the aircraft transparency.

18. A method of determining life expectancy of a laminated aircraft transparency having moisture penetration, comprising:

fabricating a laminated aircraft transparency having a moisture barrier over outer surface of the marginal edges of, and periphery of the laminated aircraft transparency;

during fabrication of the laminated aircraft transparency placing a sensor element responsive to moisture between the sheets and/or between the sheets and the moisture seal of the aircraft transparency, wherein the sensor element is a metal strip that corrodes in the presence of moisture, and ohm resistance measured increases as the corrosion of the metal strip increases;

operatively connecting sensor electronics to the sensor element to measure the ohm resistance of the sensor element that changes as a function of corrosion caused by moisture;

operatively connecting the sensor element and the sensor electronics to a power source to measure the electrical property of the sensor to determine if the sensor element is a new sensor element, an operating sensor element, a saturated sensor element, or a broken sensor element, and replacing the aircraft transparency when the sensor element is at a predetermined value.

* * * * *